US00PP13760P29

(12) United States Plant Patent
Goetz

(10) Patent No.: US PP13,760 P2
(45) Date of Patent: May 6, 2003

(54) FUCHSIA PLANT NAMED 'MARCIA'

(76) Inventor: Wolfram Goetz, Brahmsweg 3, D-89542 Hebrechtingen (DE)

( * ) Notice: Subject to any disclaimer, the term of this patent is extended or adjusted under 35 U.S.C. 154(b) by 0 days.

(21) Appl. No.: 10/200,314

(22) Filed: Jul. 22, 2002

(51) Int. Cl.[7] ..... A01H 5/00

(52) U.S. Cl. ..... Plt./300
(58) Field of Search ..... Plt./300

*Primary Examiner*—Kent Bell
(74) *Attorney, Agent, or Firm*—C. A. Whealy

(57) ABSTRACT

A new and distinct cultivar of Fuchsia plant named 'Marcia', characterized by its upright and pendulous plant habit; freely branching habit; full and dense plant growth habit; and numerous red purple and purple-colored flowers.

1 Drawing Sheet

BOTANICAL CLASSIFICATION/CULTIVAR DESIGNATION

*Fuchsia×hybrida* cultivar 'Marcia'.

BACKGROUND OF THE INVENTION

The present invention relates to a new and distinct cultivar of Fuchsia plant, botanically known as *Fuchsia×hybrida*, and hereinafter referred to by the name 'Marcia'.

The new Fuchsia is a product of a planned breeding program conducted by the Inventor in Hebrechtingen, Germany. The objective of the breeding program was to create new freely flowering Fuchsia cultivars with compact plant habit and numerous attractive flowers.

The new Fuchsia originated from a cross-pollination made by the Inventor of a proprietary selection *Fuchsia×hybrida* identified as code number 85/94, not patented, as the female, or seed, parent with an unidentified proprietary *Fuchsia×hybrida* selection, not patented, as the male, or pollen, parent. The cultivar Marcia was discovered and selected by the Inventor as a flowering plant within the progeny of the stated cross-pollination in a controlled environment in Hebrechtingen, Germany.

Asexual reproduction of the new Fuchsia by terminal cuttings taken at Hebrechtingen, Germany has shown that the unique features of this new Fuchsia are stable and reproduced true to type in successive generations.

BRIEF SUMMARY OF THE INVENTION

The cultivar Marcia has not been observed under all possible environmental conditions. The phenotype may vary somewhat with variations in environment such as temperature and daylength, without, however, any variance in genotype.

The following traits have been repeatedly observed and are determined to be the unique characteristics of 'Marcia'. These characteristics in combination distinguish 'Marcia' as a new and distinct Fuchsia cultivar:

1. Upright and cascading plant habit.

2. Freely branching habit; dense and full plant growth habit.

3. Numerous red purple and purple-colored flowers.

Sepal and petal colors of plants of the new Fuchsia are more intense than sepal and petal colors of plants of the female parent. In addition, plants of the new Fuchsia flower earlier than plants of the female parent. Plants of the new Fuchsia differ primarily from plants of the male parent in flower coloration.

Plants of the new Fuchsia can be compared to the cultivar Lucy, not patented. In side-by-side comparisons conducted in Hebrechtingen, Germany, plants of the new Fuchsia were more upright than plants of the cultivar Lucy and differed in petal coloration.

BRIEF DESCRIPTION OF THE PHOTOGRAPHS

The accompanying colored photographs illustrate the overall appearance of the new Fuchsia, showing the colors as true as it is reasonably possible to obtain in colored reproductions of this type. Colors in the photographs may differ slightly from the color values cited in the detailed botanical description which accurately describe the colors of the new Fuchsia.

The photograph at the top of the sheet comprises a side perspective view of a typical potted plant of 'Marcia'.

The photograph at the bottom of the sheet is a close-up view of a developing lateral branch, developing flower buds, fully opened flowers, and upper and lower surfaces of typical fully expanded leaves of 'Marcia'.

DETAILED BOTANICAL DESCRIPTION

The aforementioned photographs and following observations and measurements describe plants grown in Bonsall, Calif., under commercial practice during the spring in a polypropylene-covered shadehouse with day temperatures ranging from 13 to 35° C., night temperatures ranging from 13 to 18° C., and light levels about 5,000 foot-candles. Three rooted cuttings were planted per 20-cm container and plants were grown for about 12 weeks. In the following description, color references are made to The Royal Horticultural Society Colour Chart, 1995 Edition, except where general terms of ordinary dictionary significance are used.

Botanical classification: *Fuchsia×hybrida* cultivar Marcia.
Parentage:

*Female or seed parent.*—Proprietary selection of *Fuchsia×hybrida* identified as code number 85/94, not patented.

*Male, or pollen, parent.*—Unidentified proprietary selection of *Fuchsia×hybrida*, not patented.

Propagation:

*Type cutting.*—Terminal cuttings.

*Time to initiate roots.*—About 14 days at 21° C.

*Time to produce a rooted cutting.*—About 28 days at 21° C.

*Root description.*—Fine and freely-branching; white to light brown in color.

Plant description:

*Form.*—Upright and cascading plant habit. Freely branching habit; dense and full plants. Freely flowering. Moderately vigorous.

*Plant height at flowering.*—About 44 cm.

*Plant diameter at flowering.*—About 24 cm.

*Branching habit.*—Freely branching habit; typically about 18 to 20 lateral branches develop per plant. Pinching (removal of terminal apex) enhances lateral branch development.

*Lateral branch description.*—Length: About 32 cm. Diameter: About 3 mm. Internode length: About 3.6 cm. Aspect: Initially upright to cascading with flower development. Strength: Moderately strong. Texture: Sparsely pubescent. Color: 146C to 146D; towards the apex, blushed with 59C to 59D.

*Foliage description.*—Arrangement: Simple, opposite. Length: About 5.2 cm. Width: About 3.8 cm. Shape: Elliptic. Apex: Narrowly acute. Base: Attenuate to obtuse. Margin: Slightly serrulate. Texture, upper and lower surfaces: Smooth, glabrous. Venation pattern: Pinnate. Petiole length: About 2.2 cm. Petiole diameter: About 2 mm. Petiole texture, upper and lower surfaces: Smooth, glabrous. Color: Young leaves, upper surface: 137A. Young leaves, lower surface: 147B. Fully expanded leaves, upper surface: 147A. Fully expanded leaves, lower surface: 147B. Venation, upper surface: 147C. Venation, lower surface: 147B to 147C. Petiole, upper surface: 144C blushed with 181C. Petiole, lower surface: 144C.

Flower description:

*Flower type and habit.*—Single bi-colored axillary flowers. Freely flowering; potentially two flowers per leaf axil; about two to four open flowers and about six to ten flower buds per lateral branch. Flowers not persistent. Flowers not fragrant.

*Natural flowering season.*—March through October in southern California; flowering continuous during this period.

*Flower longevity.*—Flowers last about four to five days on the plant.

*Flower orientation.*—Initially upright, then pendulous.

*Flower diameter.*—About 5 cm.

*Flower height.*—About 6.5 cm.

*Flower buds.*—Shape: Ovoid. Length: About 8 mm. Width: About 3 mm. Color: 60B to 60C.

*Petals.*—Quantity: Four; arranged in a single whorl, imbricate. Length: About 2.3 cm. Width: About 2.2 cm. Shape: Fan-shaped, rounded. Apex: Rounded with cordate tendencies. Margin: Entire. Texture, upper and lower surfaces: Glabrous, smooth, satiny. Color: When opening, upper and lower surfaces: 83B; towards base, 57A. Fully opened, upper surface: 90A; color becoming closer to 80B with subsequent development; venation towards base, 57A. Fully opened, lower surface: 90B; venation towards base, 57A to 57B.

*Sepals.*—Quantity: Four; arranged in a single whorl, fused at base. Length: About 4 cm. Width: About 6 mm. Shape: Narrowly elliptic. Apex: Acute. Margin: Entire. Texture, upper and lower surfaces: Glabrous, smooth. Color: When opening, upper and lower surfaces: 58B. Fully opened, upper and lower surfaces: 58B.

*Peduncles.*—Length: About 3.5 cm. Diameter: About 1.25 mm. Aspect: Arching to horizontal. Strength: Moderately strong. Texture: Smooth, glabrous. Color: 145B.

*Reproductive organs.*—Stamens: Stamen number: Eight per flower. Anther length: About 2.5 mm. Anther diameter: About 1 mm. Anther shape: Oblong. Anther color: 59D. Pollen amount: Scarce. Pollen color: 155A. Pistils: Pistil number: One per flower. Pistil length: About 7.8 cm. Style length: About 5.5 cm. Style color: 57B to 57C. Stigma shape: Rounded. Stigma color: 57A. Ovary color: 137C.

*Seed/fruit.*—Seed and fruit production has not been observed.

Disease/pest resistance: Plants of the new Fuchsia have not been observed to be resistant to pathogens and pests common to Fuchsias.

Temperature tolerance: Plants of the new Fuchsia have been observed to tolerate low temperatures of 2° C. and high temperatures of 35° C.

Garden performance: Plants of the new Fuchsia have been observed to perform well in the garden and are tolerant to rain and wind.

It is claimed:

1. A new and distinct cultivar of Fuchsia plant named 'Marcia', as illustrated and described.

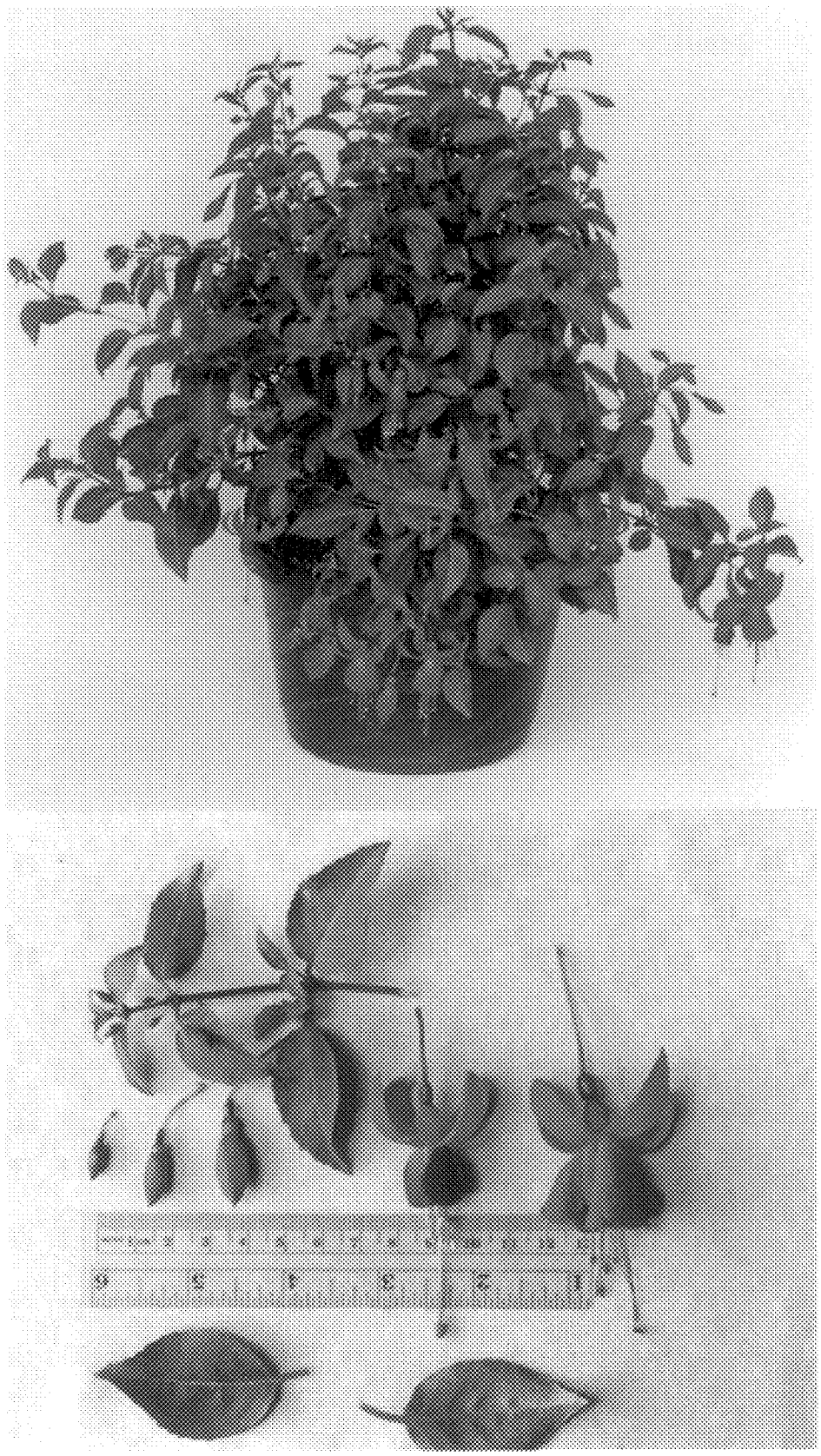

* * * * *